(12) United States Patent
Sauter et al.

(10) Patent No.: US 6,500,963 B2
(45) Date of Patent: Dec. 31, 2002

(54) PROCESS FOR PREPARING OPTICALLY ACTIVE DIHYDROPYRONES

(75) Inventors: Markus Sauter, Gensingen (DE); Burkhard Jaeger, Bingen (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/076,006

(22) Filed: Feb. 14, 2002

(65) Prior Publication Data

US 2002/0165269 A1 Nov. 7, 2002

Related U.S. Application Data

(60) Provisional application No. 60/271,359, filed on Mar. 9, 2001.

(30) Foreign Application Priority Data

Feb. 22, 2001 (DE) .......................................... 101 08 470

(51) Int. Cl.[7] ...................... C07D 307/56; C07D 311/04
(52) U.S. Cl. ........................................ 549/313; 549/417
(58) Field of Search .................................. 549/313, 417

(56) References Cited

U.S. PATENT DOCUMENTS 4,661,628 A 4/1987 Cannata et al.
6,147,095 A 11/2000 Ferry et al.

FOREIGN PATENT DOCUMENTS

| EP | 1 355 667 | 7/1970 |
|---|---|---|
| WO | WO 95/14012 | 5/1995 |
| WO | WO 95/30670 | 11/1995 |
| WO | WO 99/12919 | 3/1999 |

OTHER PUBLICATIONS

Turner, SR et al 'Tipranavir (PNU–140690): A potent, orally bioavailale nonpeptidic HIV protease inhibitor of the 5,6–dihydro–4–hydroxy–2–pyrone sulfanamide class' J. Med. Chem. 1988, 41, pp. 3467–3476.*

Thaisrivongs, S. et al; Structure–Based Design of HIV Protease Inhibitors.

XP–002088571 –J. Med. Chem. 1996, 39, 4630–4632.

* cited by examiner

*Primary Examiner*—Amelia Owens
(74) *Attorney, Agent, or Firm*—Robert P. Raymond; Anthony P. Bottino; Alan R. Stempel

(57) ABSTRACT

The invention relates to a new process for preparing optically active dihydropyrones, new intermediate products which may be obtained by this synthesis, and their use as starting compounds in the preparation of pharmaceutically active compounds.

11 Claims, No Drawings

PROCESS FOR PREPARING OPTICALLY ACTIVE DIHYDROPYRONES

RELATED APPLICATION DATA

This application claims benefit to German application 10 108 470.6 filed Feb. 22, 2001 and U.S. provisional application No. 60/271,359 filed Mar. 9, 2001.

TECHNICAL FIELD OF THE INVENTION

The invention relates to a new process for preparing optically active dihydropyrones, new intermediate products which can be obtained by this method of synthesis, and their use as starting compounds in the preparation of pharmaceutically active compounds.

BACKGROUND TO THE INVENTION 5,6-Dihydro-4-hydroxy-2-pyrones are important structural elements in a number of pharmaceutically active compounds. One category of particular interest comprises the 5,6-dihydro-4-hydroxy-2-pyrone-sulphonamides, which may be used as non-peptidic HIV-protease inhibitors. A particularly effective example of a potent and orally bioavailable HIV-protease inhibitor in this category of substances is the compound tipranavir (PNU-140690), which has the following structure

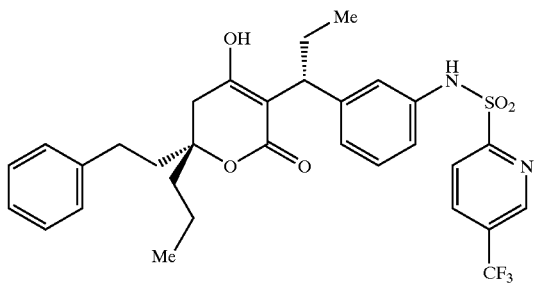

This and other structurally similar compounds are known from the prior art (cf. for example *J. Med. Chem.* 1998, 41, 3467–3476).

A key step in the synthesis of the abovementioned compounds and those structurally similar thereto is the reaction of 5,6-dihydro-4-hydroxy-2-pyrones 1 with suitably substituted carbonyl compounds 2 to form the condensation products 8, as illustrated in Diagram 1.

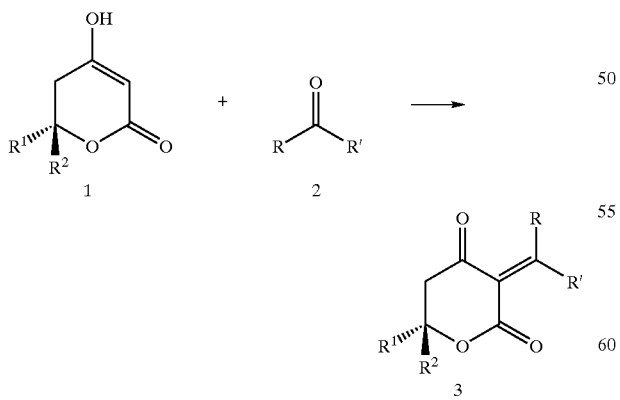

Diagram 1:

The meanings of the groups $R^1$ and $R^2$ which are different from one another can be found in the detailed description of the invention which follows. The groups may vary in their meanings depending on the substitution pattern of the respective target compounds, as described in the prior art.

It is significant according to the invention that the chiral information contained in the starting compounds 1 is retained in the subsequent reaction shown in Diagram 1, as a result of which the compounds 1 have a central importance in the synthesis of the abovementioned pharmaceutically active compounds.

The aim of the present invention is therefore to provide a process which allows 1 to be synthesised in high yields, with high enantiomeric purity, at the lowest possible technical cost and in a high space/time yield.

SUMMARY OF THE INVENTION

It is therefore an object of the invention to provide a new process for preparing optically active dihydropyrones, new intermediate products which can be obtained by this method of synthesis, and their use as starting compounds in the preparation of pharmaceutically active compounds. Each of the aforementioned is described further in the detailed description section below.

DETAILED DESCRIPTION OF THE INVENTION

Surprisingly, it has been found that these objectives of the present invention as outline above can be achieved if the chiral 5,6-dihydro-4-hydroxy-2-pyrones 1 are prepared according to the procedure illustrated in Diagram 2.

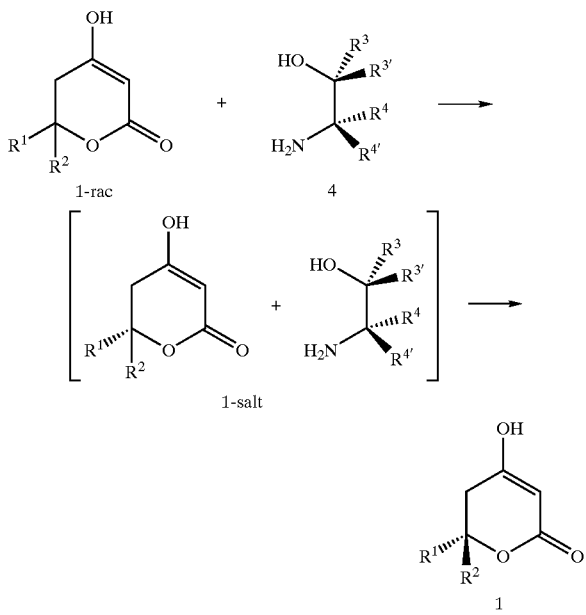

Diagram 2

For this, racemic 5,6-dihydro-4-hydroxy-2-pyrones 1-rac are converted with chiral aminoalcohols 4 into the salts 1-salt. Surprisingly, the latter can be obtained in the form of crystallising compounds and thus isolated in good yields and with a high degree of purity. Depending on the choice of the optically active aminoalcohols 4 the salts 1-salt of the R- or S-configured compounds 1 are crystallised. The salts 1-salt' of the unwanted enantiomers of 1 stay in solution during this reaction step. The optically active target compounds are liberated from the crystallised salts 1-salt.

Within the scope of the present invention any reference to compounds of formula 1 should always be taken as a reference to the optically active compounds 1, whereas any reference to compounds of formula 1-rac should be taken as a reference to the racemic mixture of the compounds of formula 1.

Accordingly, the present invention relates to a process for preparing a compound of formula 1

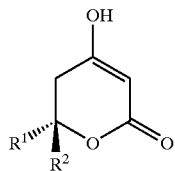

1 optionally in the form of the tautomers thereof, wherein $R^1$ and $R^2$ independently of one another denote hydrogen or a group selected from among $C_1$–$C_4$-alkyl, $C_3$–$C_8$-cycloalkyl, $C_6$–$C_{10}$-aryl and —$C_1$–$C_4$-alkylene-$C_6$–$C_{10}$-aryl, which may optionally be mono-, di- or trisubstituted by one or more groups selected from among hydroxy, halogen, $C_1$–$C_4$-alkoxy and $CF_3$, with the proviso that $R^1$ and $R^2$ cannot simultaneously have the same meaning, characterised in that in a first step a compound of formula 1-rac

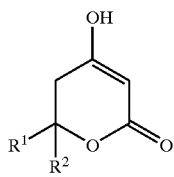

1-rac wherein $R^1$ and $R^2$ may have the meanings given hereinbefore, is reacted in a suitable solvent with one or more, preferably one chiral aminoalcohol of formula 4

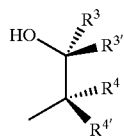

4 wherein $R^3$, $R^{3'}$, $R^4$ and $R^{4'}$ which may be identical or different denote hydrogen or a group selected from among $C_1$–$C_4$-alkyl, $C_3$–$C_8$-cycloalkyl, $C_6$–$C_{10}$-aryl and —$C_{1-C4}$-alkylene-$C_6$–$C_{10}$-aryl, which may optionally be mono-, di- or trisubstituted by one or more groups selected from among hydroxy, halogen, $C_1$–$C_4$-alkoxy, —S—$C_1$–$C_4$-alkyl, —$SO_2$–$C_1$–$C_4$-alkyl, $NO_2$ and $CF_3$, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3'}$ cannot have the same meaning, to form a salt of formula 1-salt

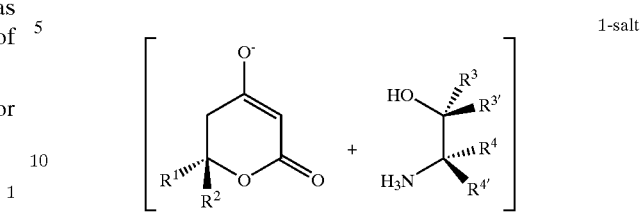

1-salt wherein the groups $R^1$, $R^2$, $R^3$, $R^{3'}$, $R^4$ and $R^{4'}$ may have the meanings given hereinbefore, the resulting crystalline compound 1-salt is isolated and the target compound is liberated therefrom.

A preferred process according to the invention is a process for preparing a compound of formula 1 optionally in the form of the tautomers thereof, wherein $R^1$ and $R^2$ independently of one another denote a group selected from among methyl, ethyl, propyl, butyl, phenyl, benzyl, phenylethyl and phenylpropyl which may optionally be monosubstituted by a group selected from among hydroxy, fluorine, chlorine, bromine, methoxy, ethoxy and $CF_3$ with the proviso that $R^1$ and $R^2$ cannot simultaneously have the same meaning, characterised in that in a first step a compound of formula 1-rac wherein $R^1$ and $R^2$ may have the meanings given hereinbefore is reacted in a suitable solvent with one or more, preferably one chiral aminoalcohol of formula 4 wherein $R^3$, $R^{3'}$, $R^4$ and $R^{4'}$ which may be identical or different denote hydrogen or a group selected from among methyl, ethyl, propyl, phenyl, benzyl and phenylethyl, which may optionally be mono- or trisubstituted by one or two groups selected from among hydroxy, fluorine, chlorine, bromine, methoxy, ethoxy, Me-S—, Me-$SO_2$—, Et-S—, Et-$SO_2$—, $NO_2$ and $CF_3$, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3'}$ cannot have the same meaning, to form a salt of formula 1-salt, wherein the groups $R^1$, $R^2$, $R^3$,$R^{3'}$,$R^4$ and $R^{4'}$ may have the meanings given hereinbefore, the resulting crystalline compound 1-salt is isolated and the target compound 1 is liberated therefrom.

Particularly preferred according to the invention is a process for preparing a compound of formula 1 optionally in the form of the tautomers thereof, wherein $R^1$ and $R^2$ independently of one another denote a group selected from among methyl, ethyl, propyl, butyl, phenyl, benzyl, phenylethyl and phenylpropyl, with the proviso that $R^1$ and $R^2$ cannot simultaneously have the same meaning, characterised in that in a first step a compound of formula 1-rac, wherein $R^1$ and $R^2$ may have the meanings given hereinbefore, is reacted in a suitable solvent with one or more, preferably one chiral aminoalcohol of formula 4 wherein $R^3$, $R^{3'}$, $R^4$ and $R^{4'}$ which may be identical or different denote hydrogen or a group selected from among methyl, ethyl, propyl, phenyl and benzyl, which may optionally be monosubstituted by a group selected from among hydroxy, methoxy, Me—S—, Me—$SO_2$—and $NO_2$, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3\prime}$ cannot have the same meaning, to form a salt of formula 1-salt, wherein the groups $R^1$, $R^2$, $R^3$, $R^{3\prime}$, $R^4$ and $R^{4\prime}$ may have the meanings given hereinbefore, the resulting crystalline compound 1-salt is isolated and the target compound 1 is liberated therefrom.

Also preferred is a process for preparing a compound of formula 1 optionally in the form of the tautomers thereof, wherein $R^1$ and $R^2$ independently of one another denote a group selected from among ethyl, propyl, butyl, benzyl, phenylethyl and phenylpropyl, with the proviso that $R^1$ and $R^2$ cannot simultaneously have the same meaning, characterised in that in a first step a compound of formula 1-rac, wherein $R^1$ and $R^2$ may have the meanings given hereinbefore, is reacted in a suitable solvent with one or more, preferably one chiral aminoalcohol of formula 4, wherein $R^3$ and $R^{3\prime}$ which may be identical or different denote hydrogen or a group selected from among phenyl, hydroxyphenyl, methylthiophenyl and nitrophenyl, and $R^4$ and $R^{4\prime}$ which may be identical or different denote hydrogen or a group selected from among methyl, hydroxymethyl and phenyl, with the proviso that if $R^3$ and $R^{3\prime}$ have the same meaning, the groups $R^4$ and $R^{4\prime}$ cannot have the same meaning, and with the proviso that if $R^4$ and $R^{4\prime}$ have the same meaning, the groups $R^3$ and $R^{3\prime}$ cannot have the same meaning, to form a salt of formula 1-salt, wherein the groups $R^1$, $R^2$, $R^3$, $R^{3\prime}$, $R^4$ and $R^{4\prime}$ may have the meanings given hereinbefore, the resulting crystalline compound 1-salt is isolated and the target compound 1 is liberated therefrom.

Particularly preferred according to the invention is a process for preparing a compound of formula 1, optionally in the form of the tautomers thereof, wherein $R^1$ denotes phenylethyl and $R^2$ denotes propyl, characterised in that in a first step a compound of formula 1-rac wherein $R^1$ and $R^2$ may have the meanings given hereinbefore is reacted in a suitable solvent with one or more, preferably one chiral aminoalcohol of formula 4 wherein $R^3$ and $R^{3\prime}$ which may be identical or different denote hydrogen or a group selected from among phenyl, methylthiophenyl and nitrophenyl, and $R^4$ and $R^{4\prime}$ which may be identical or different denote hydrogen or a group selected from among methyl, hydroxymethyl and phenyl, with the proviso that if $R^3$ and $R^{3\prime}$ have the same meaning, the groups $R^4$ and $R^{4\prime}$ cannot have the same meaning, and with the proviso that if $R^4$ and $R^{4\prime}$ have the same meaning, the groups $R^3$ and $R^{3\prime}$ cannot have the same meaning, to form a salt of formula 1-salt, wherein the groups $R^1$, $R^2$, $R^3$, $R^{3\prime}$, $R^4$ and $R^{4\prime}$ may have the meanings given hereinbefore, the resulting crystalline compound 1-salt is isolated and the target compound 1 is liberated therefrom.

The following procedure may be used to carry out the process according to the invention. To prepare 1-salt the racemic mixture 1-rac is dissolved in a suitable organic solvent, preferably in an anhydrous organic solvent, most preferably in a non-polar organic solvent. Preferred solvents according to the invention are acetonitrile, propionitrile, butyronitrile, methylene chloride, chloroform, methyl acetate, ethyl acetate, n-butyl acetate, tert-butylmethylether, isopropanol, tetrahydrofuran, dioxane, methanol or mixtures thereof, more preferably acetonitrile, propionitrile, butyronitrile, methylene chloride, n-butyl acetate or mixtures thereof, most preferably acetonitrile, propionitrile, butyronitrile or mixtures thereof.

At a temperature of $-10°$ C. to $50°$ C., preferably $0°$ C. to $40°$ C., more preferably $10-30°$ C., most preferably $20-25°$ C. the chiral amine 4 is added and the resulting mixture is mixed thoroughly by stirring for a period of 1–12 h, preferably 3–8 h, more preferably 4–6 h at constant temperature. Between 0.3 –2.0 mol, preferably 0.4 –1.0 mol, most preferably about 0.45–0.55 mol of amine 4 are used per mol of 1-rac put in. It may be helpful in some cases to add seed crystals to accelerate crystallisation or to use other methods known in the art for increasing the tendency to crystallisation.

The reaction mixture is then brought to a temperature of $-40°$ C. to $30°$ C., preferably $-20°$ C. to $20°$ C., more preferably $-10°$ C. to $15°$ C., most preferably $0°$ C. to $10°$ C. and the crystalline 1-salt is separated off. The salt which is diastereomeric to 1-salt may be obtained from the remaining solution analogously using methods known in the prior art. The crystals thus obtained are then washed with one of the abovementioned organic solvents, preferably with the organic solvent which is used to carry out the reaction, and dried in vacuo.

The following procedure may be used according to the invention to liberate the compounds of formula 1 from the 1-salt salts. The 1-salt compounds are taken up in a suitable solvent, preferably a polar solvent, more preferably in water. An organic solvent, preferably an organic, water-immiscible solvent is used for this. This solvent is preferably selected from among toluene, methyl tert.-butylether, methylene chloride, chloroform, methyl acetate, ethyl acetate, n-butyl acetate and mixtures thereof, more preferably selected from toluene, methyl tert.-butylether, ethyl acetate, n-butyl acetate and mixtures thereof, toluene and methyl tert.-butylether being of particular importance. According to the invention, the ratio in which the abovementioned polar solvent and the abovementioned water-immiscible solvent are used is in the range from 1:10 (v/v) to 10:1 (v/v), preferably 1:5 (v/v) to 5:1 (v/v), more preferably 3:1 (v/v) to 1:3 (v/v). An organic or inorganic acid is then added to this mixture, while according to the invention the use of inorganic mineral acids is preferred. The following acids are preferably used as inorganic acids: hydrochloric acid, sulphuric acid, nitric acid, formic acid, acetic acid or phosphoric acid, preferably hydrochloric acid, sulphuric acid or phosphoric acid, most preferably hydrochloric acid and sulphuric acid, while sulphuric acid is of particular importance according to the invention for performing this step of the process. The acid may be dissolved in dilute or concentrated form, in the form of aqueous solutions or in organic solvents, optionally also in gaseous form, where technically possible. If sulphuric acid is used, for example, 30% sulphuric acid (aq) may be used. It is clear to anyone skilled in the art that at least stoichiometric amounts of acid are necessary in order to liberate 1 completely from 1-salt. It is preferable according to the invention for the acid to be added in excess. In this way, a pH of <5, preferably a pH of 0.5–3, more preferably a pH of about 1–2 is obtained according to the invention.

After all the acid has been added, the mixture is stirred for between 0.25–5 h, preferably 0.5–3 h, more preferably 0.75–1.5 h. Two phases are formed. The aqueous phase is separated off and the remaining organic phase is optionally washed another one to five times with water and finally the solvent is distilled off in vacuo. As a rule, no further purification of the products is necessary. Depending on the crystallisation tendency of 1 in the solvent in question, the target compounds may also be isolated by crystallisation. By working up the organic phase, e.g. by adding a base, the amines 4 initially used in the synthesis can be recovered and recycled into a new reaction with 1-rac.

As is clear from the foregoing description of the process according to the invention, the compounds of formula 1-salt are of particular importance, due for example to the surprisingly high crystallisation tendency of these salts.

Accordingly, in another aspect, the present invention relates to the compounds of formula 1-salt

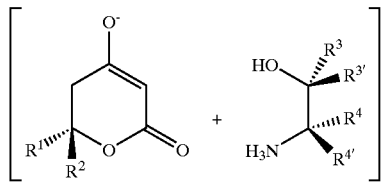

1-salt wherein
$R^1$ and $R^2$ independently of one another denote hydrogen or a group selected from among $C_1$–$C_4$-alkyl, $C_3$–$C_8$-cycloalkyl, $C_6$–$C_{10}$-aryl and —$C_1$–$C_4$-alkylene-$C_6$–$C_{10}$-aryl, which may optionally be mono-, di- or trisubstituted by one or more groups selected from among hydroxy, halogen, $C_1$–$C_4$-alkoxy and $CF_3$;

$R^3$, $R^{3'}$, $R^4$ and $R^{4'}$ which may be identical or different denote hydrogen or a group selected from among $C_1$–$C_4$-alkyl, $C_3$–$C_8$-cycloalkyl, $C_6$–$C_{10}$-aryl and —$C_1$–$C_4$-alkylene-$C_6$–$C_{10}$-aryl, which may optionally be mono-, di- or trisubstituted by one or more groups selected from among hydroxy, halogen, $C_1$–$C_4$-alkoxy, —S—$C_1$–$C_4$-alkyl, —$SO_2$—$C_1$–$C_4$-alkyl, $NO_2$ and $CF_3$, optionally in the form of the tautomers thereof, with the proviso that $R^1$ and $R^2$ cannot simultaneously have the same meaning, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3'}$ cannot have the same meaning.

Preferred compounds are those of formula 1-salt wherein
$R^1$ and $R^2$ independently of one another denote a group selected from among methyl, ethyl, propyl, butyl, phenyl, benzyl, phenylethyl and phenylpropyl which may optionally be monosubstituted by a group selected from among hydroxy, fluorine, chlorine, bromine, methoxy, ethoxy and $CF_3$;

$R^3$, $R^{3'}$, $R^4$ and $R^{4'}$ which may be identical or different denote hydrogen or a group selected from among methyl, ethyl, propyl, phenyl, benzyl and phenylethyl, which may optionally be mono- or disubstituted by one or two groups selected from among hydroxy, fluorine, chlorine, bromine, methoxy, ethoxy, Me—S—, Me—$SO_2$—, Et—S—, Et—$SO_2$—, $NO_2$ and $CF_3$, optionally in the form of the tautomers thereof, with the proviso that $R^1$ and $R^2$ cannot simultaneously have the same meaning, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3'}$ cannot have the same meaning.

Particularly preferred are compounds of formula 1-salt wherein
$R^1$ and $R^2$ independently of one another denote a group selected from among methyl, ethyl, propyl, butyl, phenyl, benzyl, phenylethyl and phenylpropyl, $R^3$, $R^{3'}$, $R^4$ and $R^{4'}$ which may be identical or different denote hydrogen or a group selected from among methyl, ethyl, propyl, phenyl and benzyl, which may optionally be monosubstituted by a group selected from among hydroxy, methoxy, Me—S—, Me—SO2—and $NO_2$, optionally in the form of the tautomers thereof, with the proviso that $R^1$ and $R^2$ cannot simultaneously have the same meaning, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3'}$ cannot have the same meaning.

Also preferred are compounds of formula 1-salt wherein
$R^1$ and $R^2$ independently of one another denote a group selected from among ethyl, propyl, butyl, benzyl, phenylethyl and phenylpropyl, $R^3$ and $R^{3'}$ which may be identical or different denote hydrogen or a group selected from among phenyl, hydroxyphenyl, methylthiophenyl and nitrophenyl;

$R^4$ and $R^{4'}$ which may be identical or different denote hydrogen or a group selected from among methyl, hydroxymethyl and phenyl, optionally in the form of the tautomers thereof, with the proviso that $R^1$ and $R^2$ cannot simultaneously have the same meaning, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3'}$ cannot have the same meaning.

Also particularly preferred according to the invention are compounds of formula 1-salt
wherein
$R^1$ denotes phenylethyl and $R^2$ denotes propyl, $R^3$ and $R^{3'}$ which may be identical or different denote hydrogen or a group selected from among phenyl, methylthiophenyl and nitrophenyl, and $R^4$ and $R^{4'}$ which may be identical or different denote hydrogen or a group selected from among methyl, hydroxymethyl and phenyl, optionally in the form of their tautomers, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3'}$ cannot have the same meaning.

Because of the central importance of the compounds of formula 1-salt as starting compounds for synthesising optically active, pharmaceutically active compounds, in a further aspect the invention relates to the use of compounds of general formula 1-salt for preparing pharmaceutically active compounds. Preferably, the present invention relates to the use of compounds of formula 1-salt for preparing tipranavir.

The present invention further relates to processes for preparing pharmaceutically active compounds which are characterised in that compounds of formula 1-salt are used which may be obtained by the process according to the invention for preparing 1-salt.

The present invention preferably relates to processes for preparing tipranavir which are characterised in that compounds of formula 1-salt are used which may be obtained by the process for preparing 1-salt according to the invention.

Moreover, one aspect of the present invention relates to the use of compounds of general formula 1 which are obtained according to the present invention for preparing pharmaceutically active compounds. The present invention preferably relates to the use of compounds of formula 1 which are obtained according to the present invention for the preparation of tipranavir.

The present invention further relates to methods of preparing pharmaceutically active compounds which are characterised in that compounds of formula 1 are used which are obtained by the process according to the invention for preparing 1.

The present invention preferably relates to processes for preparing tipranavir which are characterised in that compounds of formula 1 are used which are obtained by the process according to the invention for preparing 1.

According to the invention, the compounds 1-salt may be synthesised starting from the compounds of formula 1-rac. The latter may be obtained by the procedure outlined in Diagram 3.

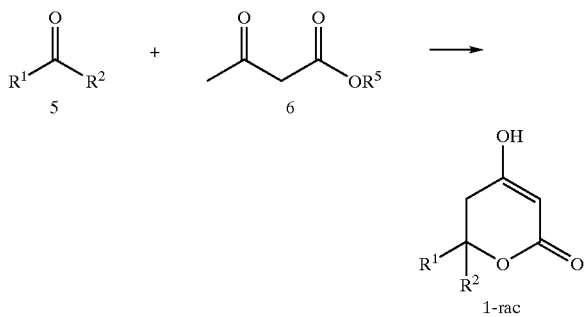

Diagram 3:

For this, a suitably substituted carbonyl compound wherein the groups $R^1$ and $R^2$ may have the meanings given hereinbefore is reacted with an acetoacetic acid derivative 6 wherein $R^5$ denotes $C_1$–$C_4$-alkyl or a cation selected from among lithium, sodium and potassium, preferably sodium, preferably methyl, ethyl, propyl or sodium, most preferably ethyl or sodium, to obtain the compound 1-rac, wherein the groups $R^1$ and $R^2$ may have the meanings given hereinbefore.

This reaction is carried out in the presence of organic or inorganic bases, preferably in the presence of organic, sterically demanding bases. Within the scope of the present invention it is preferable to use organic bases which are selected from among DBU and DBN. Sterically demanding organic bases in the sense of the present invention also include organometallic compounds such as lithium, sodium and potassium salts of secondary amines. Preferred bases of this type are selected from among lithium diisopropylamine, lithium diethylamine, lithium hexamethyldisilazane, sodium hexamethyldisilazane, potassium hexamethyidisilazane or lithium tert.-butoxide, preferably lithium diisopropylamine, lithium diethylamine, lithium hexamethyldisilazane, sodium hexamethyldisilazane, potassium hexamethyldisilazane, particularly preferably lithium diisopropylamine, and lithium diethylamine. These latter bases are either commercially obtainable or may be synthesised by methods known in the art.

In order to prepare the compounds of formula 1-rac according to the invention, one of the abovementioned bases, which is either generated in situ or used directly, is placed in a suitable organic solvent, preferably in an organic anhydrous solvent. The solvents used are preferably ethereal solvents such as tetrahydrofuran (THF), methylethylether, diethylether, dioxane or other non-polar organic solvents such as toluene, hexane or heptane. If desired, the ethereal solvents may also be used in admixture with the abovementioned non-polar solvents. It is preferable to use the abovementioned ethereal solvents. The solvent THF and mixtures containing it, preferably THF/hexane or THF/toluene, are of particular importance.

The solution thus obtained is cooled, preferably to a temperature of below 0° C., preferably below −10° C., more preferably below −20° C. According to the invention, it is particularly preferred to carry out the reaction in a range from −78° C. to −40° C. If one of the abovementioned solvents is not in a liquid aggregate state at these temperatures, the lowest possible reaction temperature is determined by the flow point of the solvent used, as will be clear to anyone skilled in the art. The acetoacetic acid derivative 6, in which $R^5$ may be as hereinbefore defined, is then added to the cooled solution of the base in one of the abovementioned solvents. At most stoichiometric amounts of 6 are added per mol of base used. Preferably, substoichiometric amounts of 6 are used, the molar ratio of 6 to the base used preferably being in the range from 0.9:1 to 0.2:1, more preferably 0.7:1–0.3:1, most preferably 0.6:1–0.4:1.

After the addition of 6 the mixture is stirred at constant temperature for a period of about minutes to 1 h and a solution of 5 in one of the abovementioned solvents, preferably in the same organic solvent, is slowly added dropwise thereto. A maximum of 1 mol of 5 is used per mol of compound 6 used. Preferably, substoichiometric amounts of are used, the molar ratio of to 6 preferably being in the range from 0.9:1–0.2:1, more preferably 0.8:1–0.3:1, most preferably 0.7:1–0.5:1. After the addition is complete, stirring is continued either at constant temperature or at slightly elevated temperature. If the temperature is increased it is still preferably kept below 0° C., preferably below −10° C., more preferably below −20° C. It is particularly preferable according to the invention to carry out the reaction in a range from −40C to −20° C. According to the invention, the reaction lasts in the region of 0.5–8 h, preferably 1–5 h, most preferably 1.5–3 h.

The reaction may be stopped by methods known in the art, e.g. by the addition of aqueous solutions, e.g. aqueous ammonium chloride solution. The reaction mixture is also worked up analogously to the procedures known in the prior art.

Examples of alkyl groups (including those which are part of other groups) include, unless otherwise specified, branched and unbranched alkyl groups with 1 to 4 carbon atoms. The following hydrocarbon groups are mentioned by way of example: methyl, ethyl, propyl, 1-methylethyl (Isopropyl), n-butyl, 1-methylpropyl, 2-methylpropyl, 1,1-dimethylethyl (tert.butyl). The definitions propyl and butyl in each case include the associated isomeric groups. In some cases, the common abbreviations Me for methyl, Et for ethyl, Prop for propyl and But for butyl are used for the abovementioned alkyl groups.

Examples of alkylene groups include branched and unbranched alkylene bridges with 1 to 4 carbon atoms. These may be, for example: methylene, ethylene, propylene and butylene. Unless otherwise specified, the terms propylene and butylene used above also include all the possible isomeric forms. Accordingly, the term propylene includes the isomeric bridges n-propylene, methylethylene and dimethylmethylene and the term butylene includes the isomeric bridges n-butylene, 1-methylpropylene, 2-methylpropylene, 1,1-dimethylethylene and 1,2-dimethylethylene.

Cycloalkyl generally denotes a saturated cyclic hydrocarbon group with 3 to 8 carbon atoms. Cyclic hydrocarbons with 3 to 6 carbon atoms are preferred. Cyclopropyl, cyclobutyl, cyclopentyl, cyclohexyl, cycloheptyl and cyclooctyl are mentioned as examples.

Alkyloxy, which may optionally also be referred to as alkoxy, generally denotes a straight-chain or branched alkyl group with 1 to 4 carbon atoms bound via an oxygen atom. The methoxy group is particularly preferred.

The term aryl denotes an aromatic ring system with 6 to 10 carbon atoms. Preferred aryl groups are naphthyl and phenyl, the phenyl group being particularly preferred. Naphthyl may be abbreviated to Naph and phenyl to Ph.

By aryl-alkylene or alkylene-aryl are meant, for the purposes of the invention, aryl groups linked by an alkylene bridge, the alkylene groups and aryl groups being defined as mentioned above. Unless otherwise specified, preferred alkylene-aryl groups according to the invention are benzyl, 2-phenylethyl and 3-phenylpropyl.

Halogen within the scope of the present invention denotes fluorine, chlorine, bromine or iodine, of which fluorine, chlorine and bromine are preferred, unless otherwise specified.

Within the scope of the present invention any reference to compounds of formula 1 should be taken as a reference to the compound in an optically active form. The particular optically active form is determined by the definition of the groups $R^1$ and $R^2$ in each case. Any reference to 1 includes all the enantiomeric mixtures of the two possible enantiomers of 1 which are not racemic. Racemic mixtures are referred to as 1-rac, as hereinbefore defined. Any reference to 1 also includes the particular tautomeric forms of 1.

Within the scope of the present invention any reference to compounds of formula 1-salt should be taken as a reference to the compound in an optically active form. The particular optically active form is determined by the definition of the groups $R^1$, $R^2$, $R^3$, $R^{3'}$, $R^4$ and $R^{4'}$. Any reference to 1-salt includes all the diastereomeric mixtures of the possible diastereomers of 1-salt which are not racemic. Any reference to 1-salt also includes the particular tautomeric forms of 1-salt.

The following Examples serve to illustrate some methods of synthesis carried out by way of example for preparing tiotropium bromide. They are to be understood only as descriptions of possible methods given as examples, without restricting the invention to their contents.

Preparation of the Compound of Formula 1-rac
(Wherein $R^1$ Denotes 2-Phenylethyl and $R^2$ denotes n-Propyl)

104 ml (1.00 mol) of diethylamine in 160 ml THF are cooled to −50° C. Within 10 minutes, 400 ml (1.00 mol) of a 2.5 M n-BuLi solution in n-hexane are added to this solution. After it has all been added, stirring is continued for another 10 min and 63 ml (0.500 mol) of acetoacetic acid ester are then added. After 10 minutes, 60 g (0.340 mol) of 1-phenylhexan-3-one in 80 ml of THF are added dropwise over 30 min at −50° C. The mixture is heated to −30° C. and stirred for another 2 h. The reaction solution is added to 1200 ml of saturated $NH_4Cl$ solution, the aqueous phase is separated off and the organic phase is washed with 400 ml of saturated $NH_4Cl$ solution and 200 ml of 2N HCl. Then the organic phase is washed until neutral with $NaHCO_3$ solution, separated off and the solvent is distilled off in vacuo. The oil obtained (118 g) is combined at ambient temperature with a solution of 29.4 g (1.20 mol) of KOH (85%) in 140 ml of MeOH. After the reaction has ended (about 10h) the MeOH is separated off by distillation. The residue is taken up in 400 ml of water and 400 ml of toluene and after phase separation the aqueous phase is extracted again with 400 ml of toluene. The aqueous phase is adjusted to pH <2 with 136 ml of 30% $H_2SO_4$ and extracted with 400 ml of toluene. The toluene phase is washed three times with 200 ml of water. The toluene is evaporated down to about half the volume. The residue is mixed with 500 ml of octane and stirred until crystallisation occurs. 67.5 g (76%) of the compound 1-rac are obtained.

Preparation of the Compound of Formula 1-salt
(Wherein $R^1$ Denotes 2-Phenylethyl, $R^2$ Denotes n-Propyl, $R^3$ Denotes Hydrogen, $R^{3'}$ Denotes 4-Methylthiophenyl, $R^4$ Denotes Hydroxymethyl and $R^{4'}$ Denotes Hydrogen)

29 g (110 mmol) of the compound 1-rac obtained by the above method are dissolved in 250 ml of acetonitrile. After the addition of 10.6 g (50.0 mmol) of (+)-thiomicamine 4 a solution is formed. It is stirred for hours at ambient temperature, cooled to about 5° C. and the crystals are suction filtered through a Büchner funnel. The crystals obtained are washed with 150 ml of acetonitrile. The crystals are dried in a vacuum drying cupboard for 12 h. 21.3 g (90% yield based on the amine 4 used) of colourless crystals are obtained. The ratio of diastereomers is about 90:10 without any further crystallisation. If necessary, the optical purity can be increased by a further crystallisation step.

Preparation of the Compound of Formula 1
(Wherein $R^1$ Denotes 2-Phenylethyl and $R^2$ Denotes n-Propyl)

29 g (110 mmol) of the compound 1-salt obtained by the method described above are combined with 290 methyl-tert.-butylether in 290 ml of water. ml of 30% sulphuric acid are added thereto (pH=1.5). After one hour's stirring, two phases are formed. The aqueous phase is separated off. The organic phase is washed three times with 100 ml of water. Then the organic phase is evaporated down in vacuo to leave a residue. 14.0 g (yield 88%) of compound 1 are obtained.

Table 1 lists the compounds of formula 1-salt obtained by the method according to the invention.

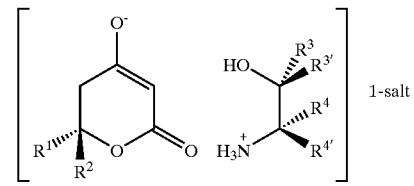

| Example | $R^1$ | $R^2$ | $R^3$ | $R^{3'}$ | $R^4$ | $R^{4'}$ |
|---|---|---|---|---|---|---|
| 1 | Ph-ethyl- | n-propyl- | H | 4-MeS-Ph- | HO-methyl- | H |
| 2 | n-propyl- | Ph-ethyl- | Ph | H | Me | H |
| 3 | n-propyl- | Ph-ethyl- | H | Ph | H | Me |
| 4 | Ph-ethyl- | n-propyl- | H | H | H | Ph |
| 5 | Ph-ethyl- | n-propyl- | H | H | Ph | H |
| 6 | Ph-ethyl- | n-propyl- | H | Ph | HO-methyl- | H |
| 7 | Ph-ethyl- | n-propyl- | Ph | H | H | HO-methyl- |
| 8 | Ph-ethyl- | n-propyl- | H | 4-$NO_2$-Ph | HO-methyl- | H |
| 9 | Ph-ethyl- | n-propyl- | 4-$NO_2$-Ph | H | H | HO-methyl- |
| 10 | n-propyl- | Ph-ethyl- | Ph | H | Ph | H |

-continued

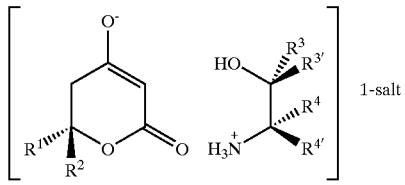

| Example | $R^1$ | $R^2$ | $R^3$ | $R^{3'}$ | $R^4$ | $R^{4'}$ |
|---|---|---|---|---|---|---|
| 11 | n-propyl- | Ph-ethyl- | H | Ph | H | Ph |

What is claimed is:

1. A process for preparing a compound of formula 1

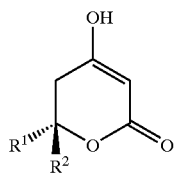

1 optionally in the form of the tautomers thereof,
wherein
 $R^1$ and $R^2$ independently of one another denote hydrogen or a group selected from $C_1$–$C_4$-alkyl, $C_3$–$C_8$-cycloalkyl, $C_6$–$C_{10}$-aryl and —$C_1$–$C_4$-alkylene-$C_6$–$C_{10}$-aryl, which may optionally be mono-, di- or trisubstituted by one or more groups selected from hydroxy, halogen, $C_1$–$C_4$-alkoxy and $CF_3$, with the proviso that $R^1$ and $R^2$ cannot simultaneously have the same meaning, comprising:
wherein a first step reacting a compound of formula 1-rac

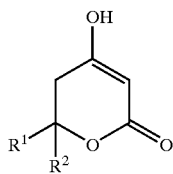

1-rac wherein $R^1$ and $R^2$ may have the meanings given in this claim, in a suitable solvent with one or more chiral aminoalcohol of formula 4

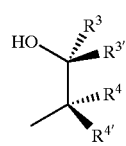

4 wherein
 $R^3$, $R^{3'}$, $R^4$ and $R^{4'}$ which may be identical or different denote hydrogen or a group selected from $C_1$–$C_4$-alkyl, $C_3$–$C_8$-cycloalkyl, $C_6$–$C_{10}$-aryl and —$C_1$–$C_4$-alkylene-$C_6$–$C_{10}$-aryl, which may optionally be mono-, di- or trisubstituted by one or more groups selected from hydroxy, halogen, $C_1$–$C_4$-alkoxy, —S—$C_1$–$C_4$-alkyl, —$SO_2$—$C_1$–$C_4$-alkyl, $NO_2$ and $CF_3$, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3'}$ cannot have the same meaning, to form a salt of formula 1-salt

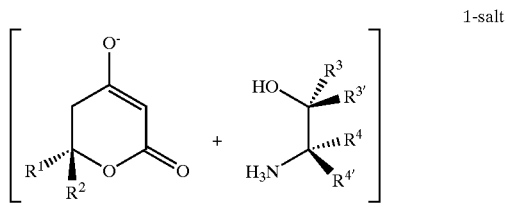

1-salt wherein the groups $R^1$, $R^2$, $R^3$, $R^{3'}$, $R^4$ and $R^{4'}$ may have the meanings given hereinbefore, isolating the resulting crystalline compound 1-salt and subsequently isolating the target compound of the formula 1 therefrom.

2. The process for preparing a compound of formula 1 optionally in the form of the tautomers thereof, according to claim 1,
wherein
 $R^1$ and $R^2$ independently of one another denote a group selected from methyl, ethyl, propyl, butyl, phenyl, benzyl, phenylethyl and phenylpropyl which may optionally be monosubstituted by a group selected from hydroxy, fluorine, chlorine, bromine, methoxy, ethoxy and $CF_3$ with the proviso that $R^1$ and $R^2$ cannot simultaneously have the same meaning,
 $R^3$, $R^{3'}$, $R^4$ and $R^{4'}$ which may be identical or different denote hydrogen or a group selected from methyl, ethyl, propyl, phenyl, benzyl and phenylethyl, which may optionally be mono- or disubstituted by one or two groups selected from hydroxy, fluorine, chlorine, bromine, methoxy, ethoxy, Me-S—, Me-$SO_2$—, Et-S—, Et-$SO_2$—, $NO_2$ and $CF_3$, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3'}$ cannot have the same meaning.

3. The process for preparing a compound of formula 1, optionally in the form of the tautomers thereof, according to claim 2,
wherein
 $R^1$ and $R^2$ independently of one another denote a group selected from methyl, ethyl, propyl, butyl, phenyl, benzyl, phenylethyl and phenylpropyl, with the proviso that $R^1$ and $R^2$ cannot simultaneously have the same meaning, $R^3$, $R^{3'}$, $R^4$ and $R^{4'}$ which may be identical or different denote hydrogen or a group selected from methyl, ethyl, propyl, phenyl and benzyl, which may optionally be monosubstituted by a group selected from hydroxy, methoxy, Me—S—, Me—SO$_2$—and NO$_2$, with the proviso that if R$^3$ and R$^{3'}$ have the same meaning, the groups R$^4$ and R$^{4'}$ cannot have the same meaning, and with the proviso that if R$^4$ and R$^{4'}$ have the same meaning, the groups R$^3$ and R$^{3'}$ cannot have the same meaning.

4. The process for preparing a compound of formula 1, optionally in the form of the tautomers thereof, according to claim 3, wherein R$^1$ and R$^2$ independently of one another denote a group selected from ethyl, propyl, butyl, benzyl, phenylethyl and phenylpropyl, with the proviso that R$^1$ and R$^2$ cannot simultaneously have the same meaning, R$^3$ and R$^{3'}$ which may be identical or different denote hydrogen or a group selected from phenyl, hydroxyphenyl, methylthiophenyl and nitrophenyl, and R$^4$ and R$^{4'}$ which may be identical or different denote hydrogen or a group selected from methyl, hydroxymethyl and phenyl, with the proviso that if R$^3$ and R$^{3'}$ have the same meaning, the groups R$^4$ and R$^{4'}$ cannot have the same meaning, and with the proviso that if R$^4$ and R$^{4'}$ have the same meaning, the groups R$^3$ and R$^{3'}$ cannot have the same meaning.

5. The process for preparing a compound of formula 1, optionally in the form of the tautomers thereof, according to claim 4, wherein R$^1$ denotes phenylethyl and R$^2$ denotes propyl, R$^3$ and R$^{3'}$ which may be identical or different denote hydrogen or a group selected from phenyl, methylthiophenyl and nitrophenyl, and R$^4$ and R$^{4'}$ which may be identical or different denote hydrogen or a group selected from methyl, hydroxymethyl and phenyl, with the proviso that if R$^3$ and R$^{3'}$ have the same meaning, the groups R$^4$ and R$^{4'}$ cannot have the same meaning, and with the proviso that if R$^4$ and R$^{4'}$ have the same meaning, the groups R$^3$ and R$^{3'}$ cannot have the same meaning.

6. The process according to claims 1, 2, 3, 4 or wherein there is one chiral aminoalcohol of formula 4.

7. A compound of formula 1-salt

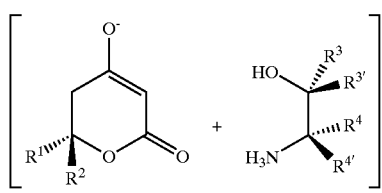

wherein

R$^1$ and R$^2$ independently of one another denote hydrogen or a group selected from C$_1$–C$_4$-alkyl, C$_3$–C$_8$-cycloalkyl, C$_6$–C$_{10}$-aryl and —C$_1$–C$_4$-alkylene-C$_6$–C$_{10}$-aryl, which may optionally be mono-, di- or trisubstituted by one or more groups selected from hydroxy, halogen, C$_1$–C$_4$-alkoxy and CF$_3$;

R$^3$, R$^{3'}$, R$^4$ and R$^{4'}$ which may be identical or different denote hydrogen or a group selected from C$_1$–C$_4$-alkyl, C$_3$–C$_8$-cycloalkyl, C$_6$–C$_{10}$-aryl and —C$_1$–C$_4$-alkylene-C$_6$–C$_{10}$-aryl, which may optionally be mono-, di- or trisubstituted by one or more groups selected from hydroxy, halogen, C$_1$–C$_4$-alkoxy, —S—C$_1$–C$_4$-alkyl, —SO$_2$—C$_1$–C$_4$-alkyl, NO$_2$ and CF$_3$, optionally in the form of the tautomers thereof, with the proviso that R$^1$ and R$^2$ cannot simultaneously have the same meaning, with the proviso that if R$^3$ and R$^{3'}$ have the same meaning, the groups R$^4$ and R$^{4'}$ cannot have the same meaning, and with the proviso that if R$^4$ and R$^{4'}$ have the same meaning, the groups R$^3$ and R$^{3'}$ cannot have the same meaning.

8. The compound of formula 1-salt according to claim 7, wherein

R$^1$ and R$^2$ independently of one another denote a group selected from methyl, ethyl, propyl, butyl, phenyl, benzyl, phenylethyl and phenylpropyl which may optionally be monosubstituted by a group selected from hydroxy, fluorine, chlorine, bromine, methoxy, ethoxy and CF$_3$;

R$^3$, R$^{3'}$, R$^4$ and R$^{4'}$ which may be identical or different denote hydrogen or a group selected from methyl, ethyl, propyl, phenyl, benzyl and phenylethyl, which may optionally be mono- or disubstituted by one or two groups selected from hydroxy, fluorine, chlorine, bromine, methoxy, ethoxy, Me-S—, Me—SO$_2$—, Et-S—, Et-SO$_2$—, NO$_2$ and CF$_3$, optionally in the form of the tautomers thereof, with the proviso that R$^1$ and R$^2$ cannot simultaneously have the same meaning, with the proviso that if R$^3$ and R$^{3'}$ have the same meaning, the groups R$^4$ and R$^{4'}$ cannot have the same meaning, and with the proviso that if R$^4$ and R$^{4'}$ have the same meaning, the groups R$^3$ and R$^{3'}$ cannot have the same meaning.

9. The compound of formula 1-salt according to claim 8, wherein

R$^1$ and R$^2$ independently of one another denote a group selected from methyl, ethyl, propyl, butyl, phenyl, benzyl, phenylethyl and phenylpropyl, R$^3$, R$^{3'}$, R$^4$ and R$^{4'}$ which may be identical or different denote hydrogen or a group selected from methyl, ethyl, propyl, phenyl and benzyl, which may optionally be monosubstituted by a group selected from hydroxy, methoxy, Me-S—, Me-SO$_2$—and NO$_2$, optionally in the form of the tautomers thereof, with the proviso that R$^1$ and R$^2$ cannot simultaneously have the same meaning, with the proviso that if R$^3$ and R$^{3'}$ have the same meaning, the groups R$^4$ and R$^{4'}$ cannot have the same meaning, and with the proviso that if R$^4$ and R$^{4'}$ have the same meaning, the groups R$^3$ and R$^{3'}$ cannot have the same meaning.

10. The compound of formula 1-salt according to claim 9, wherein

R$^1$ and R$^2$ independently of one another denote a group selected from ethyl, propyl, butyl, benzyl, phenylethyl and phenylpropyl, R$^3$ and R$^{3'}$ which may be identical or different denote hydrogen or a group selected from phenyl, hydroxyphenyl, methylthiophenyl and nitrophenyl;

R$^4$ and R$^{4'}$ which may be identical or different denote hydrogen or a group selected from methyl, hydroxymethyl and phenyl, optionally in the form of the tautomers thereof, with the proviso that R$^1$ and R$^2$ cannot simultaneously have the same meaning, with the proviso that if R$^3$ and R$^{3'}$ have the same meaning, the groups R$^4$ and R$^{4'}$ cannot have the same meaning, and with the proviso that if R$^4$ and R$^{4'}$ have the same meaning, the groups R$^3$ and R$^{3'}$ cannot have the same meaning.

11. The compound of formula 1-salt according to claim 10, wherein
- $R^1$ denotes phenylethyl and $R^2$ denotes propyl,
- $R^3$ and $R^{3'}$ which may be identical or different denote hydrogen or a group selected from phenyl, methylthiophenyl and nitrophenyl, and
- $R^4$ and $R^{4'}$ which may be identical or different denote hydrogen or a group selected from methyl, hydroxymethyl and phenyl, optionally in the form of the tautomers thereof, with the proviso that if $R^3$ and $R^{3'}$ have the same meaning, the groups $R^4$ and $R^{4'}$ cannot have the same meaning, and with the proviso that if $R^4$ and $R^{4'}$ have the same meaning, the groups $R^3$ and $R^{3'}$ cannot have the same meaning.

* * * * *